United States Patent [19]

Waters

[11] 4,347,746
[45] Sep. 7, 1982

[54] TESTING OF SHIPPING CONTAINERS

[76] Inventor: Kevin R. Waters, 1 Little St., Maroubra, New South Wales, Australia, 2035

[21] Appl. No.: 66,460

[22] Filed: Aug. 14, 1979

[30] Foreign Application Priority Data

Apr. 2, 1978 [AU] Australia .............................. PD8258

[51] Int. Cl.³ ........................... G01L 5/00; G01M 5/00
[52] U.S. Cl. ......................................... 73/789; 73/786
[58] Field of Search .......................... 73/789, 760, 786

[56] References Cited

U.S. PATENT DOCUMENTS

| 886,691 | 5/1908 | Fowler | 73/760 X |
|---|---|---|---|
| 1,708,333 | 4/1929 | Smith | 73/786 |
| 2,295,249 | 9/1942 | Yates | 73/789 |
| 3,545,262 | 12/1970 | Steele et al. | 73/825 |
| 3,871,213 | 3/1975 | Jureit et al. | 73/825 |

FOREIGN PATENT DOCUMENTS 1264752 2/1972 United Kingdom ................. 73/789

OTHER PUBLICATIONS

Publ. "Stress-Analysis Method?" N. A. Crites, pp. 90-96, Product Engineering, Oct. 16, 1961.

Primary Examiner—Daniel M. Yasich
Attorney, Agent, or Firm—Harness, Dickey & Pierce

[57] ABSTRACT

An apparatus and method for testing the load bearing characteristics of a shipping container comprising a device for supporting a load so that the load can be inserted into the container through open doors at one end thereof, an arrangement for elevating the container so that the load is transferred from the supporting device to the container, structure for supporting the container in the elevated position when the elevating arrangement is lowered and measuring any stresses or strains in the container while it is under load.

7 Claims, 3 Drawing Figures

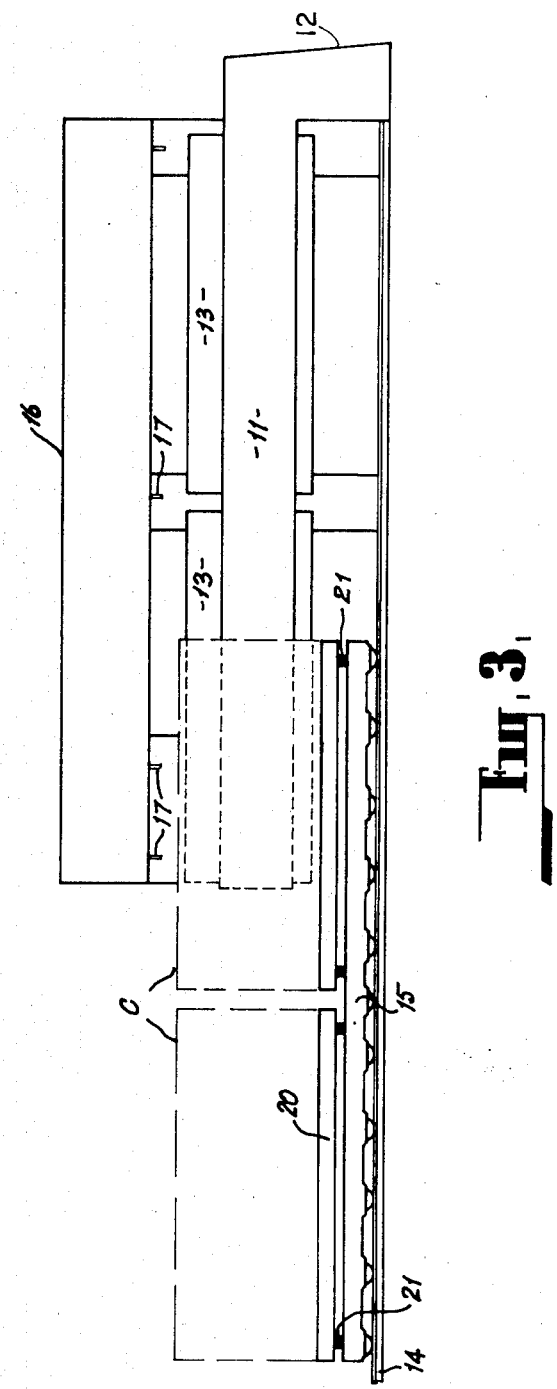

TESTING OF SHIPPING CONTAINERS

This invention relates to the testing of shipping containers to ensure that they are capable of carrying a predetermined load.

At the present, cargo handling equipment such as slings, grabs, and the like are subjected to regular testing to ensure that they are not deteriorated and are capable of supporting a predetermined load. Shipping containers are not subjected to such testing because a simple means of testing is not available.

The object of the present invention is to provide such a means of testing which is relatively safe in use.

The invention resides in a means for testing the load bearing characteristics of a shipping container comprising means for supporting a load so that the load can be inserted into the container through open doors at one end at one end of the container, means for elevating the container so that the load is transferred from the supporting means to the container, means for supporting the container in the elevated position when the elevating means are lowered and means for measuring any stresses or strains in the container whilst it is under load.

The invention will be better understood by reference to the following description when read in conjunction with the accompanying diagrammatic drawings wherein:

FIG. 3 is a side elevation showing the container being positioned to receive the load supporting means.

Figure 1:
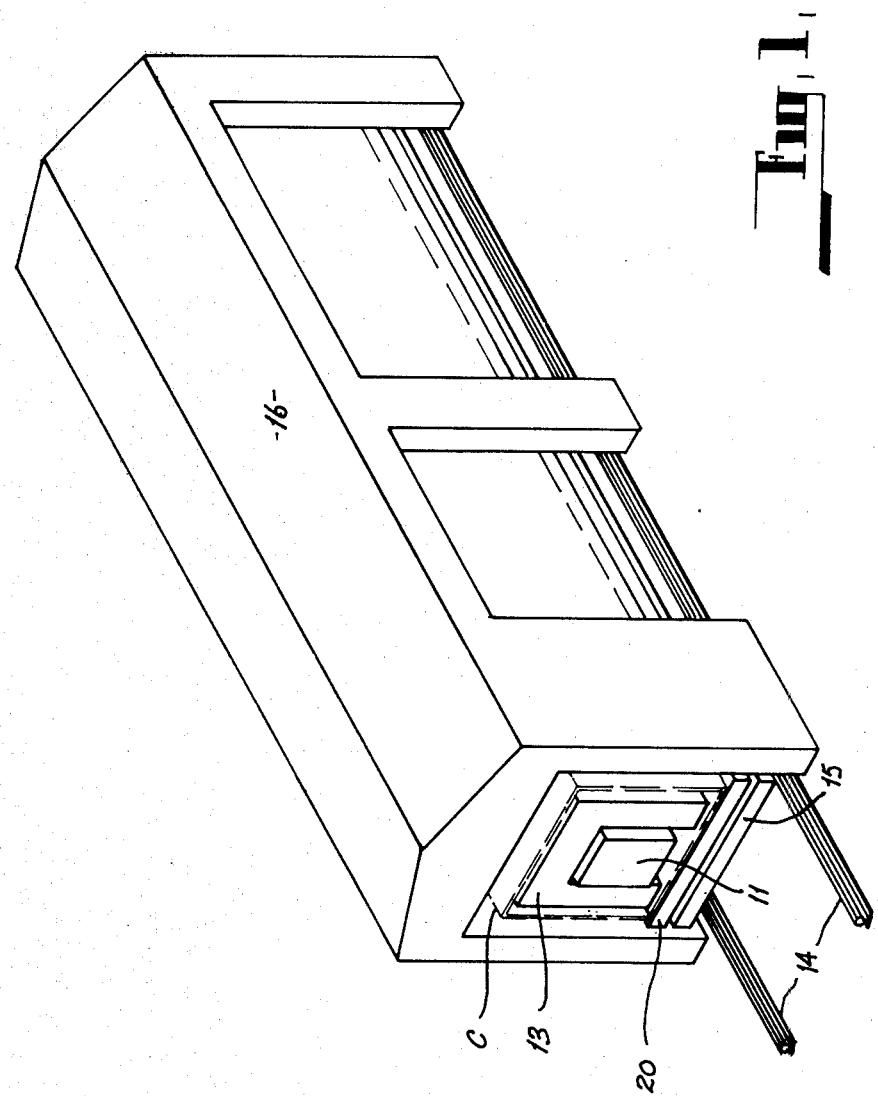
FIG. 1 is a perspective view of the testing apparatus embodying this invention showing the container (in broken lines) in the position prior to elevation.
Figure 2:
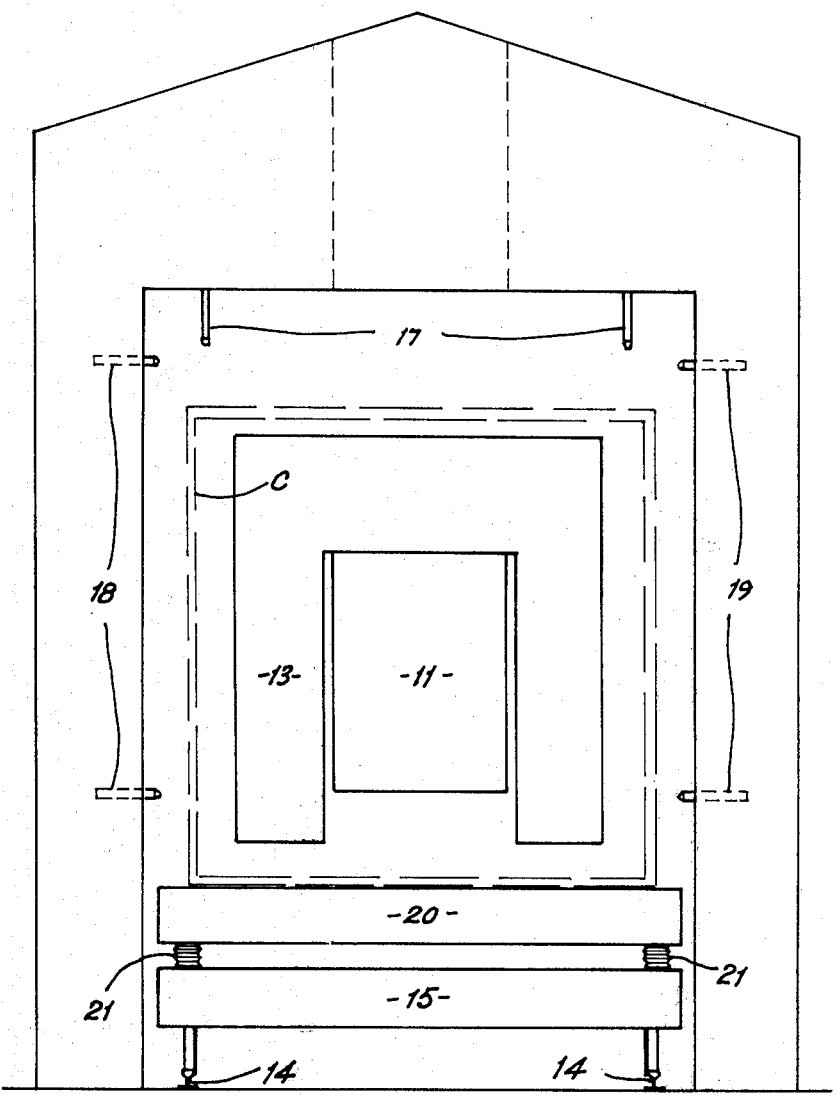
FIG. 2 is an end elevation of the testing apparatus.

As shown in the drawings the test load supporting means comprises an elongated beam 11 anchored at one end to a supporting structure 12 so that it projects therefrom in a substantially horizontal cantilevered position. A substantially inverted U-shaped test load 13 of a size appropriate to the size of the container to be tested is mounted on the beam in a saddle like fashion as is best seen in FIG. 2 As will be seen in FIG. 3 of the drawings the test load 13 is in two segments. It may be formed in any number of segments so that the load can be readily varied by removing one or more segments. The beam is positioned above a track 14 on which a carriage 15 is mounted by roller wheels or the like for movement relative to the beam 11. The track is aligned with the test load supporting beam 11 which is surmounted by a container supporting structure 16 provided with conventional twist locks 17, 18 and 19 for engaging a container in the usual manner. The container to be tested identified by reference C and shown in broken lines is mounted on a platform 20 carried by the carriage 15. Air bags 21 or other suitable elevating means such as hydraulic or screw jacks or scissors are positioned between the carriage 15 and the platform 20 to enable the platform to be raised.

In operation the container C to be tested is positioned on the platform 20 with the carriage 15 clear of the test load supporting structure. The platform 20 and the associated container C is provided with suitable guides (not shown) for correctly positioning the continers C and the doors at the end of the container C adjacent the test load supporting structure 12. The carriage 15 is then moved into position under the test load supporting structure 12 with the load on the test load supporting beam 11 entering the container through the open doors. Means (not shown) are provided for correctly positioning the carriage with respect to the test load supporting structure 12. The platform 20 is then elevated by actuating the airbags 21 or other lifting devices to lift the container C to a position in which it can be engaged by one of the sets of twist locks 17, 18 or 19. This action provides one test for the alignment of the container C. If the container C is out of square the twist locks will not properly engage the container C.

As the container C is lifted it engages the load 13 and lifts it clear of the test load supporting beam 11. After the twist locks 17, 18 or 19 have engaged the container C the platform 20 is lowered by acturating the airbags 21 or other lifting devices leaving the container C suspended from one of the sets of twist locks 17, 18 or 19. Strain gauges or photogrammetric means or other suitable measuring devices of conventional design are used to test the strength of the container C. If desired the container C may be tested whilst supported from the top set of twist locks 17 or one of the two side sets 18 and 19.

If it is desired to test the container C under a rolling load wheels may be provided on the underside of the load 13.

When the tests have been completed the platform 20 is raised and the twist locks 17, 18 or 19 disengaged. As the container C is lowered the load engages the test load supporting beam 11 after which the carriage can be run clear of the test load supporting structure and then the container C lifted off.

In the embodiment described above the supporting beam 11 remains in position so that it will receive and support the load 13 if a container C should fail when under test.

In some instances it may be desired to test a container C with the doors closed. In this case the test load supporting structure is located at the other end of the track remote from the test load supporting beam. The container C is run into position with the doors open at one end and the platform 20 elevated so that the load is engaged by the container C and lifted clear of the test load supporting beam. The carriage is then moved clear of the test load supporting beam with the load in the container C and the doors closed. The carriage is then moved into position under the container supporting structure 16 and tested. The operation is then reversed to return the load to its position on the supporting beams.

I claim:

1. Means for testing the load bearing characteristics of a shipping container having doors at at least one end thereof comprising supporting means mounted at one end in a supporting housing for supporting a test load so that the test load and said supporting means can be received in the container through open doors at one end thereof, means for moving the test load supporting means and the container relative to each other in a longitudinal direction for placing the container around the test load, elevating means for elevating the container so that the test load is transferred from said supporting means to the container, support means in said supporting housing for supporting the container in the elevated position when the elevating means are lowered and means for measuring stresses or strains in the container whilst it is under load and in said elevated condition.

2. Means as claimed in claim 1 wherein the container is supported on a platform mounted on a carriage running on a track aligned with the load supporting means, and the elevating means are positioned between the platform and the carriage.

3. Means as claimed in claim 2 wherein the elevating means comprises air bags.

4. Means as claimed in anyone of claims 1, 2 or 3 wherein the test load is in the form of a plurality of removable segments.

5. Means as claimed in claim 4 wherein the load is supported on the load supporting means in a saddle like fashion.

6. Means as claimed in claim 5 wherein the test load is fitted with wheels or rollers to enable a test under a rolling test load to be conducted.

7. Means as claimed in claim 6 wherein the means for supporting the container comprises one or more sets of twist locks for supporting the container from the top or from each side, said sets of twist locks being fitted to a supporting structure.

* * * * *